United States Patent
Belt et al.

(10) Patent No.: US 10,251,629 B2
(45) Date of Patent: *Apr. 9, 2019

(54) IMAGING SYSTEM FOR IMAGING A PERIODICALLY MOVING OBJECT

(71) Applicant: KONINKLIJKE PHILIPS N.V., Eindhoven (NL)

(72) Inventors: Harm Jan Willem Belt, Weert (NL); Steven Antonie Willem Fokkenrood, 's-Hertogenbosch (NL); Fei Zuo, Eindhoven (NL); Alexander Franciscus Kolen, Eindhoven (NL); Szabolcs Deladi, Veldhoven (NL); Godefridus Antonius Harks, Rijen (NL)

(73) Assignee: Koninklijke Philips N.V., Eindhoven (NL)

( * ) Notice: Subject to any disclaimer, the term of this patent is extended or adjusted under 35 U.S.C. 154(b) by 861 days.

This patent is subject to a terminal disclaimer.

(21) Appl. No.: 14/384,162

(22) PCT Filed: Mar. 20, 2013

(86) PCT No.: PCT/IB2013/052218
§ 371 (c)(1),
(2) Date: Sep. 10, 2014

(87) PCT Pub. No.: WO2013/140353
PCT Pub. Date: Sep. 26, 2013

(65) Prior Publication Data
US 2015/0038842 A1 Feb. 5, 2015

Related U.S. Application Data

(60) Provisional application No. 61/614,544, filed on Mar. 23, 2012.

(51) Int. Cl.
*A61B 8/08* (2006.01)
*A61B 8/00* (2006.01)
(Continued)

(52) U.S. Cl.
CPC .......... *A61B 8/5276* (2013.01); *A61B 8/0858* (2013.01); *A61B 8/0883* (2013.01);
(Continued)

(58) Field of Classification Search
CPC ... A61B 8/5276; A61B 8/5284; A61B 8/5207; A61B 8/486; A61B 8/0858; A61B 8/465;
(Continued)

(56) References Cited

U.S. PATENT DOCUMENTS 5,090,413 A * 2/1992 Yoshioka ............... A61B 8/06
600/441
6,224,553 B1 * 5/2001 Nevo ..................... A61B 8/08
600/437
(Continued)

FOREIGN PATENT DOCUMENTS

WO WO2004099814 A1 11/2004
WO WO2011001309 A1 1/2011

OTHER PUBLICATIONS

Ketterline et al., "Prospective ECG-gated Mouse Cardiac Imaging with a 34-MHz Annular Array Transducer". IEEE Trans Ultrason Ferroelectr Freq Control. Jul. 2009; 56(7): 1394-1404.*
(Continued)

*Primary Examiner* — Pascal M Bui Pho
*Assistant Examiner* — Colin T Sakamoto

(57) ABSTRACT

The invention relates to an imaging system for imaging a periodically moving object. An assigning unit (18) assigns ultrasound signals like A-lines to motion phases based on a provided phase signal, wherein an ultrasound images generation unit (19) generates several ultrasound images like
(Continued)

gated M-mode images for the different motion phases based on the ultrasound signals assigned to the respective motion phase. A selecting unit (20) is used to select an ultrasound image from the generated ultrasound images, wherein a display unit (21) displays the selected ultrasound image. The selected ultrasound image corresponds therefore to a single motion phase only such that motion artifacts in the displayed ultrasound image are reduced. The imaging system is particularly useful for, for instance, monitoring cardiac ablation procedures.

13 Claims, 13 Drawing Sheets

(51) Int. Cl.
| | | |
|---|---|---|
| *A61B 18/14* | (2006.01) | |
| *A61B 8/12* | (2006.01) | |
| *A61B 18/00* | (2006.01) | |
| *A61B 90/00* | (2016.01) | |

(52) U.S. Cl.
CPC ............... *A61B 8/12* (2013.01); *A61B 8/463* (2013.01); *A61B 8/465* (2013.01); *A61B 8/486* (2013.01); *A61B 8/5284* (2013.01); *A61B 18/1492* (2013.01); *A61B 2018/00011* (2013.01); *A61B 2018/00982* (2013.01); *A61B 2018/00994* (2013.01); *A61B 2090/378* (2016.02); *A61B 2090/3782* (2016.02); *A61B 2090/3784* (2016.02)

(58) Field of Classification Search
CPC ......... A61B 8/12; A61B 8/0883; A61B 8/461; A61B 8/543; A61B 8/463; A61B 18/1492
See application file for complete search history.

(56) References Cited

U.S. PATENT DOCUMENTS

| | | | |
|---|---|---|---|
| 7,606,402 B2* | 10/2009 | Heimdal | A61B 8/00 |
| | | | 382/128 |
| 7,951,083 B2 | 5/2011 | Sui | |
| 8,317,714 B2* | 11/2012 | Hendriks | A61B 5/021 |
| | | | 600/440 |
| 2005/0203399 A1 | 9/2005 | Vaezy | |
| 2006/0178665 A1* | 8/2006 | Sloan | A61B 18/1477 |
| | | | 606/41 |
| 2007/0066898 A1* | 3/2007 | Hendriks | A61B 5/021 |
| | | | 600/437 |
| 2010/0145197 A1 | 6/2010 | Stapf | |
| 2010/0168573 A1* | 7/2010 | Sherrill | A61B 8/0883 |
| | | | 600/440 |
| 2010/0185088 A1* | 7/2010 | Perrey | A61B 8/08 |
| | | | 600/443 |
| 2011/0044522 A1* | 2/2011 | Fancourt | G06T 7/2033 |
| | | | 382/131 |
| 2012/0004547 A1 | 1/2012 | Harks | |

OTHER PUBLICATIONS

Shung, Diagnostic Ultrasound: Imaging and Blood Flow Measurements. 2006.*

Alfonso V. et al., "ECG Beat Detection Using Filter Banks", IEEE Transactions on Biomedical Engineering, vol. 46, No. 2, pp. 192 to 202, Feb. 1999.

Smith A.M.S. et al, "Texture Based Feature Extraction: Application to Burn Scar Detection in Earth Observation Satellite Sensor Imagery", International Journal of Remote Sensing, 2002, vol. 23, No. 8, pp. 1733-1739.

Freund Y. et al., "A Decision—Theoretic Generalization of On-Line Learning and an Application to Boosting", Journal of Computer and System Sciences, vol. 55, pp. 119-139, 1997.

"Improved Cardiac Gating for Medical Imaging", IP.com Disclosure Number: IPCOM000192581D, Publication Date: Jan. 25, 2010.

* cited by examiner

IMAGING SYSTEM FOR IMAGING A PERIODICALLY MOVING OBJECT

CROSS-REFERENCE TO PRIOR APPLICATIONS

This application is the U.S. National Phase application under 35 U.S.C. § 371 of International Application Serial No. PCT/IB2013/052218, filed on Mar. 20, 2013, which claims the benefit of U.S. Application Ser. No. 61/614,544, filed on Mar. 23, 2012. These applications are hereby incorporated by reference herein.

FIELD OF THE INVENTION

The invention relates to an imaging system, an imaging method and an imaging computer program for imaging a periodically moving object.

BACKGROUND OF THE INVENTION

US 2012/004547 A1 discloses a monitoring apparatus for monitoring an ablation procedure. The monitoring apparatus comprises an ultrasound image providing unit for providing an M-mode image of cardiac tissue during an ablation procedure such that a physician can control the ablation procedure based on the M-mode image.

Due to cardiac motion the M-mode image may comprise motion artifacts, which can reduce the quality of controlling the ablation procedure based on the M-mode image.

SUMMARY OF THE INVENTION

It is an object of the present invention to provide an imaging system, an imaging method and an imaging computer program for imaging a periodically moving object, which allows providing an image of the object comprising less motion artifacts.

In a first aspect of the present an imaging system for imaging a periodically moving object is presented, wherein the imaging system comprises:

an ultrasound signals providing unit for providing ultrasound signals of the object for different times, a phase signal providing unit for providing a phase signal being indicative of motion phases of a periodic movement of the object at the different times, an assigning unit for assigning the ultrasound signals to the motion phases based on the provided phase signal, an ultrasound images generation unit for generating several ultrasound images for the different motion phases, wherein an ultrasound image for a motion phase is generated based on the ultrasound signals assigned to the respective motion phase, a selecting unit for selecting an ultrasound image from the generated ultrasound images, and a display unit for displaying the selected ultrasound image.

Since the ultrasound images generation unit generates an image for a motion phase based on the ultrasound signals assigned to the respective motion phase, wherein the selecting unit selects an ultrasound image from the generated ultrasound images and wherein the display unit displays the selected ultrasound image, the selected ultrasound image corresponds to a single motion phase only such that motion artifacts in the displayed ultrasound image are reduced.

The ultrasound signals providing unit is preferentially adapted to provide A-lines of the object as the ultrasound signals. The ultrasound signals providing unit is preferentially further adapted to apply an envelope detection procedure on the A-lines and to provide the resulting A-line envelopes as the ultrasound signals. In particular, the ultrasound images generation unit is adapted to generate several M-mode images for the different motion phases, wherein an M-mode image for a motion phase is generated from the A-lines, in particular, the A-line envelopes, assigned to the respective motion phase. The several M-mode images generated for the different motion phases can be regarded as being gated M-mode images.

Preferentially, the ultrasound signals are provided temporally consecutively, wherein, if an actual ultrasound signal has been provided, the actual ultrasound signal can be assigned to a corresponding motion phase and the actual ultrasound signal can then be used to update the ultrasound image, which corresponds to the motion phase, to which the actual ultrasound signal has been assigned. For instance, if the ultrasound signals are A-lines and if the generated ultrasound images are gated M-mode images, the respective actual A-line can be assigned to a motion phase, wherein then the actual A-line can be appended to the gated M-mode image, which corresponds to the motion phase, to which the actual A-line has been assigned.

The ultrasound signals providing unit can be an ultrasound signal measuring unit for measuring the ultrasound signals of the object for different times, in particular, for measuring A-lines. Thus, the ultrasound signals providing unit can comprise one or several ultrasound transducers for sending ultrasound pulses out to and into the object and for receiving dynamic echo series after the ultrasound pulses have been reflected by the object. The ultrasound signal, in particular, the respective A-line, is then generated depending on the received dynamic echo series. The object is preferentially tissue, especially cardiac tissue, wherein the ultrasound pulses are sent into the cardiac tissue and the dynamic echo series are received from the cardiac tissue such that the generated ultrasound signal is indicative of properties of the cardiac tissue in different depths.

The ultrasound signals providing unit can also be a storing unit, in which the already measured ultrasound signals are stored, or the ultrasound signals providing unit can be a receiving unit for receiving the ultrasound signals and for providing the received ultrasound signals.

The phase signal providing unit can be a phase signal measuring unit for measuring a phase signal being indicative of motion phases of a periodic movement of the object at the different times, at which the ultrasound signals have been measured. However, also the phase signal providing unit can be a storing unit, in which the measured phase signal is stored already, or a receiving unit for receiving the measured phase signal and for providing the received phase signal.

The imaging system can therefore comprise measurement components for measuring ultrasound signals and/or phase signals, or the imaging system can be a computing system, which does not comprise measuring components, wherein in the latter case the ultrasound signals providing unit and the phase signal providing unit are storing units or receiving units, respectively, of the computer system.

The selecting unit can be adapted to allow a user to select an ultrasound image from the generated ultrasound images and/or to automatically select an ultrasound image from the generated ultrasound images. In particular, the selecting unit can be adapted to provide a graphical user interface allowing a user to select an ultrasound image from the generated ultrasound images. In an embodiment the selecting unit is adapted to determine selection values for the generated ultrasound images, wherein a selection value is determined based on the image values of the respective ultrasound image, and to apply selection rules to the selection values for automatically selecting an ultrasound image from the generated ultrasound images. The selection rules are preferentially predefined and stored in the selecting unit. In an embodiment the selecting unit is adapted to allow a user to modify selection rules or to add new selection rules.

It is preferred that the object is a tissue wall to which energy is applied for influencing the tissue wall such that the ultrasound signals providing unit provides ultrasound signals of the tissue wall for different times, wherein the selecting unit is adapted to determine at least one of the following selection values: a first distance value being indicative of a distance between a sensing probe used for measuring the ultrasound signals and the tissue wall, a wall thickness value being indicative of a thickness of the tissue wall, a transmurality value being indicative of a part of the tissue wall having been influenced by the application of energy, a second distance value being indicative of a distance between the tissue wall and an element behind the tissue wall, and a gas formation value being indicative of an amount of gas formed in the tissue wall. The transmurality value is preferentially defined as being the ratio between i) the distance of the boundary of a lesion, which has been created by applying energy to the tissue wall, to the outside of the tissue wall and ii) the wall thickness value. These selection values can be important during an ablation procedure, in which energy like radio frequency (RF) energy is applied to the tissue wall for ablating the same. Selecting an ultrasound image based on at least one of these selection values can therefore lead to a displayed image showing aspects being important to be monitored during an ablation procedure. This can result in an improved control of the ablation procedure based on the displayed selected ultrasound image.

Preferentially the selecting unit is adapted to select the ultrasound image, for which at least one of the following values has been determined: the smallest first distance value, the average first distance value, the smallest wall thickness value, the largest transmurality value, the largest second distance value, the smallest second distance value and the largest gas formation value.

During the measurement of the ultrasound signals the spatial relation between an ultrasound sensing direction, in which the ultrasound pulses are sent into the tissue wall and in which dynamic echo series are received from the tissue wall, and the tissue wall itself can vary due to the periodic movement of the tissue wall. Because of this varying spatial relation between the ultrasound sensing direction and the tissue wall, the different ultrasound images can show different tissue wall properties, for instance, they can show different wall thicknesses, different distances between a sensing probe used for measuring the ultrasound signals and the tissue wall, different levels of transmurality, different distances between the tissue wall and an element behind the tissue wall, and different gas formation values.

If the ultrasound image is selected depending on the wall thickness value, preferentially the ultrasound image having the smallest wall thickness value is selected, because the ultrasound image showing the smallest wall thickness value most likely shows the real wall thickness.

If the ultrasound image is selected based on the first distance value, preferentially the ultrasound image having the smallest first distance value is selected, because this ultrasound image corresponds most likely to the best contact between the sensing probe used for measuring the ultrasound signals and the object. However, in an embodiment, in which an energy application unit like an RF ablation electrode is integrated in the sensing probe for applying energy to the object, the ultrasound image may be selected, which has an average first distance value, because, if the ultrasound image shown on the display unit indicates the smallest distance between the tissue wall and the sensing probe or the largest distance between the tissue wall and the sensing probe, a user like a physician may apply too less or too much force, respectively, for forcing the sensing probe against the tissue wall. Thus, selecting the ultrasound image, for which the average first distance value has been determined, can guide the user to apply the correct force. In order to select the ultrasound image in accordance with the average first distance value, the ultrasound image, for which a median first distance value has been determined can be selected, or the ultrasound image can be selected, for which a first distance value has been determined, which is closest to an arithmetic average of all first distance values determined for the ultrasound images.

If the ultrasound image is selected based on the transmurality value, preferentially the ultrasound image, for which the largest transmurality value has been determined, is selected, because if a user applying energy to the object applies the energy based on this selected ultrasound image, a transmural application of the energy completely through the tissue wall and to underlying adjacent tissue can most likely be prevented.

If the second distance value is used for selecting an ultrasound image, preferentially the ultrasound image, for which the largest second distance value has been determined, is selected, because this ultrasound image most likely allows a user to distinguish between the tissue wall, to which energy should be applied, and adjacent tissue, to which energy should not be applied, thereby further improving the control of the application of energy to the tissue wall based on the selected ultrasound image.

If the gas formation value is used for selecting an ultrasound image, preferentially an ultrasound image is selected, for which the largest gas formation value has been determined, because, if a physician looks at this selected ultrasound image during an energy application procedure, gas formation is most reliably be shown, thereby allowing the physician to, for instance, halt the application of the energy, when gas formation is observed or becomes to pronounced. This can prevent gas formation inside the tissue wall and, thus, a so-called tissue pop.

In a preferred embodiment the energy is applied to the tissue wall in accordance with an energy application procedure having different stages, wherein the selecting unit is adapted such that the selection rules define the selection of an ultrasound image depending on the determined selection values and depending on the current stage of the energy application procedure. Thus, for each stage of applying energy to the object one or several ultrasound images can be selected and displayed, which allow for an optimized monitoring of the application of the energy in the respective stage. This adaptation of the selection and displaying of the one or several ultrasound image to the respective stage of applying energy to the object can further improve the monitoring of the energy application.

In particular, the selection rules can define that i) in a first stage before applying energy to the object firstly an ultrasound image is selected, for which an average first distance value has been determined, and secondly an ultrasound image is selected, for which the smallest wall thickness value has been determined, ii) in a second stage during applying energy to the object at least one of an ultrasound image, for which the largest transmurality value has been determined, and an ultrasound image, for which the largest gas formation value has been determined, is selected, and iii) in a third stage after applying energy to the object an ultrasound image, for which the largest transmurality value has been determined, is selected. Preferentially, if in the second stage several ultrasound images show a similar highest transmurality value, from these ultrasound images, which all show a similar highest transmurality value, the ultrasound image is selected, which has the largest second distance value, i.e. which shows the largest separation between the tissue wall, to which energy is applied, and an adjacent tissue structure. This further increases the likelihood that adjacent tissue is not damaged during the application of energy, if a physician applying the energy monitors the application of the energy based on the selected ultrasound image.

The imaging system is preferentially adapted to continuously provide ultrasound signals, assign the ultrasound signals to the motion phases, generate the ultrasound images and display the generated ultrasound images, wherein the ultrasound images generation unit is adapted to, after initial ultrasound images have been generated, update the ultrasound images based on the actually provided ultrasound signals, and the display unit is adapted to display the updated ultrasound images temporally consecutively for showing an updated periodic movement of the object. In particular, the ultrasound signals providing unit is preferentially adapted to continuously provide A-lines as the ultrasound signals, wherein the images generation unit is adapted to generate gated M-mode images as the ultrasound images, wherein, after initial gated M-mode images have been generated, the gated M-mode images are updated by appending actually provided A-lines and wherein the display unit is adapted to display the updated gated M-mode images temporally consecutively for showing an updated periodic movement of the object.

The assigning unit can be adapted to subdivide a motion period into the motion phases such that they have different durations depending on the phase signal. For instance, if the phase signal is a cardiac movement signal, the assigning unit can be adapted such that the duration of a motion phase including the diastole, when the heart muscles are at rest, is larger than the duration of a motion phase including the systole.

The assigning unit can be adapted to assign the ultrasound signals to motion phases of a respective motion period, after the respective motion period has been completed. The assigning unit can also be adapted to assign the ultrasound signals of a motion period of the object to the motion phases based on the phase signal provided for a previous motion period. Thus, the ultrasound signals can be assigned to a motion phase, before the actual motion period has been completed. This allows assigning the ultrasound signals to the motion phases with very low latency such that the ultrasound images generation unit can generate actual ultrasound images for the different motion phases, which include the last provided ultrasound signals, with very low latency. For instance, temporally consecutively A-lines can be provided as the ultrasound signals, wherein the actual provided A-line can be assigned to a motion phase based on a subdivision of the previous motion period into motion phases. The actual A-line can then be appended to the gated M-mode image, which corresponds to the motion phase to which the actual A-line has been assigned.

The assigning unit can be adapted to reassign the ultrasound signals of a respective motion period of the object, which have been assigned to the motion phases based on the phase signal for a previous motion period, based on the phase signal of the respective motion period, after the respective motion period has been completed, wherein the ultrasound images generation unit can be adapted to generate the ultrasound images based on the reassigned ultrasound signals, wherein the selecting unit can be adapted to select an ultrasound image from the actually generated ultrasound image and wherein the display unit can be adapted to display the selected ultrasound image. The initial approximate assignment of the ultrasound signals to the motion phases, which were based on a previous motion period, can therefore be corrected, after the respective motion period has been completed, thereby providing an accurate assignment of the ultrasound signals to the motion phases and, thus, a high quality image of the object, wherein the actually acquired, latest ultrasound signals can still be shown with very low latency.

The selecting unit can be adapted to determine a segment of the respective A-line having an ultrasound signal value below a noise threshold and to determine the wall thickness values based on the determined segment of the respective A-line. Moreover, the selecting unit can be adapted to apply a texture classification technique to the respective ultrasound image, in particular, to the respective M-mode image, for determining the wall thickness value. Also for determining the second distance value and the gas formation value the selecting unit can be adapted to use, for instance, a texture classification technique. For determining the transmurality value the selecting unit can be adapted to determine the depth within the tissue wall, to which the application of energy has influenced the tissue, by evaluating the tissue elasticity from a correlation or strain analysis between temporally consecutive A-lines, wherein the transmurality value can be determined based on this determined depth and the determined wall thickness value.

The imaged object is preferentially a region of a living being, wherein the phase signal providing unit is adapted to provide at least one of a cardiac motion signal being indicative of cardiac motion and a respiratory motion signal being indicative of respiratory motion as the phase signal. Thus, the selected and displayed image can have less motion artifacts, in particular, no motion artifacts at all, which may generally be caused by cardiac motion and/or respiratory motion.

If the phase signal providing unit provides a cardiac motion signal and a respiratory motion signal, each ultrasound signal, in particular, each A-line, can be assigned to a cardiac phase and in addition to a respiratory phase, wherein several ultrasound images for different combinations of cardiac motion phases and respiratory motion phases can be generated, wherein an ultrasound image can be generated for a combination of a cardiac motion phase and a respiratory motion phase based on the ultrasound signals, in particular the A-lines, assigned to the respective combination.

The cardiac motion signal can be an electrocardiography signal from, for example, electrocardiography surface leads attached to the breast of the living being. Alternatively or in addition, the ultrasound signals providing unit can be integrated in a catheter, in particular, into a tip of the catheter, wherein also an electrode for measuring a cardiac signal can be integrated in the catheter, especially in the catheter tip. The phase signal providing unit can also be pulse oximeter detector that can be clipped onto a finger or an earlobe, wherein the pulse oximeter detector provides the cardiac signal. The respiratory motion signal can be, for instance, an airflow signal produced by a tracheal intubation device. A respiratory signal may also be generated from a bio-impedance signal that may be measured via electrocardiography electrodes. The phase signal providing unit can also be adapted to determine the phase signal from the ultrasound signals and to provide the determined phase signal. In particular, the phase signal, which can also be regarded as being a trigger signal, can be taken from an A-line envelope by using, for instance, a Fourier analysis or a correlation analysis in a lateral direction, i.e. in the direction of the temporal axis of the M-mode image formed by the A-line envelopes. Thus, the phase signal may be determined without necessary requiring a further measuring device like an electrocardiograph, which may simplify the handling of the imaging system.

The imaging system preferentially comprises a sensing probe, in which the ultrasound signals providing unit and an energy application unit for applying energy to the object are integrated. The sensing probe is preferentially a catheter, in which at least a part of the ultrasound signals providing unit, for instance, one or several ultrasound transducers, and at least a part of the energy application unit, for instance, an ablation electrode, are integrated. Thus, a single sensing probe may be provided, which can be used for applying energy to the object, in particular, for performing a cardiac ablation procedure, and for monitoring the application of the energy by using ultrasound.

In a further aspect of the present invention an imaging method for imaging a periodically moving object is presented, wherein the imaging method comprises:

providing ultrasound signals of the object for different times by an ultrasound signals providing unit, providing a phase signal being indicative of motion phases of a periodic movement of the object at the different times by a phase signal providing unit, assigning the ultrasound signals to the motion phases based on the provided phase signal by an assigning unit, generating several ultrasound images for the different motion phases by an ultrasound images generation unit, wherein an ultrasound image for a motion phase is generated based on the ultrasound signals assigned to the respective motion phase, selecting an ultrasound image from the generated ultrasound images by a selecting unit, and displaying the selected ultrasound image by a display unit.

In a further aspect of the present invention a computer program for imaging a periodically moving object is presented, wherein the computer program comprises program code means for causing an imaging apparatus as defined in claim 1 to carry out the steps of the imaging method as defined in claim 14, when the computer program is run on a computer controlling the imaging apparatus.

It shall be understood that the imaging system of claim 1, the imaging method of claim 14 and the computer program claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
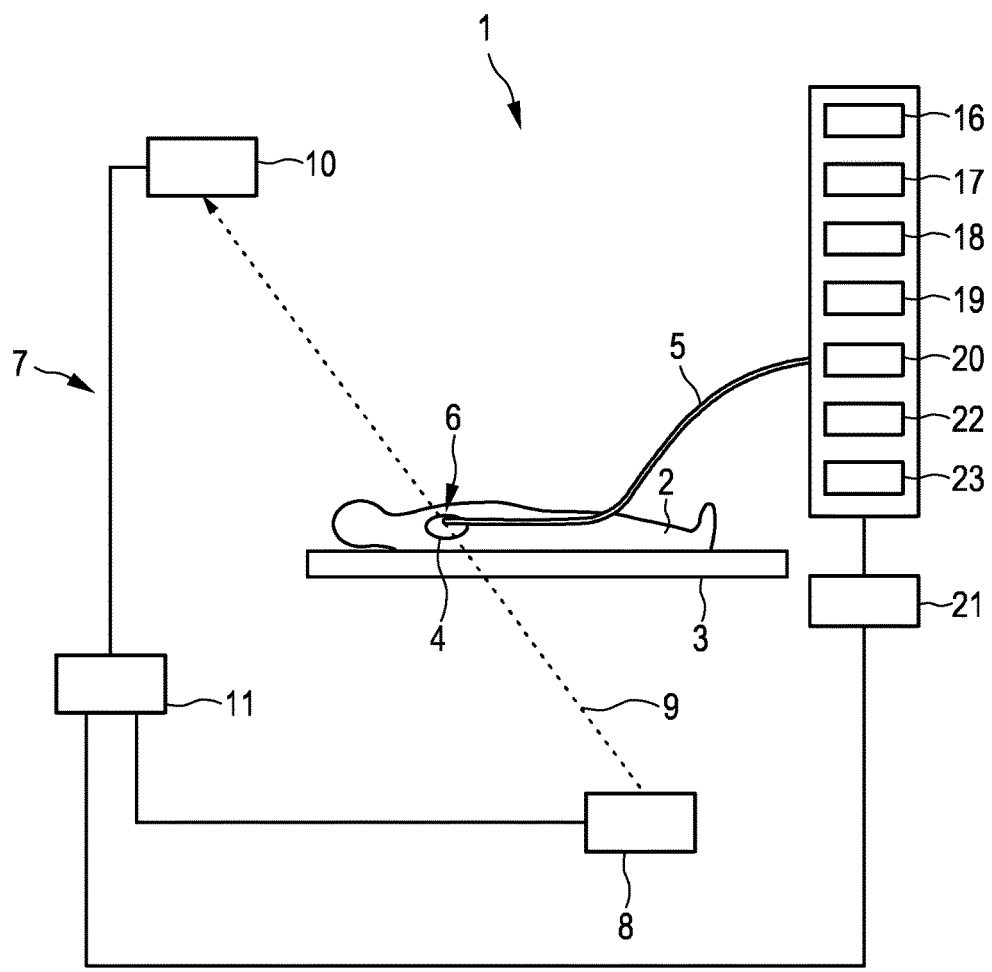
FIG. 1 shows schematically and exemplarily an embodiment of an imaging system for imaging a periodically moving object.
Figure 2:
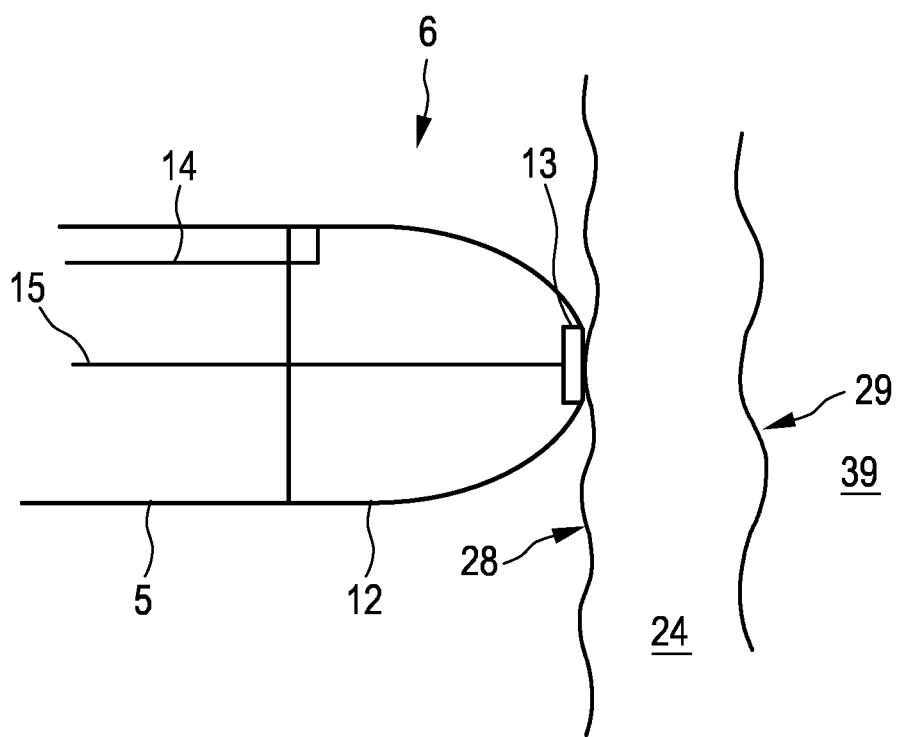
FIG. 2 shows schematically and exemplarily an embodiment of a tip of a catheter of the imaging system.

FIG. 1 shows schematically and exemplarily an imaging system 1 for imaging a periodically moving object. In this embodiment, the periodically moving object is a tissue wall of a heart 4 of a person 2 lying on a table 3. The imaging system 1 comprises a catheter 5 with a catheter tip 6, which is shown in more detail in FIG. 2.

The catheters tip 6 comprises an ultrasound transducer 13, which is connected to an ultrasound control unit 16 for controlling the ultrasound transducer 13 via an electrical connection 15 like an insulated wire. The ultrasound transducer 13 and the ultrasound control unit 16 form an ultrasound signals providing unit for providing ultrasound signals of the tissue wall 24 for different times. In particular, the ultrasound transducer 13 and the ultrasound control unit 16 are adapted to send ultrasound pulses into the tissue wall 24, to receive echo series after the ultrasound pulses have been reflected by the tissue wall 24 and to generate A-lines depending on the received echo series. The ultrasound signals providing unit 13, 16 acquires therefore temporally consecutively A-lines for providing ultrasound signals of the tissue wall 24 for different times, i.e. to each A-line a time can be assigned being the time at which the respective ultrasound pulse has been sent and received by the ultrasound signals providing unit 13, 16.

The ultrasound signals providing unit 13, 16 can preferentially be operated in an ultrasound transmission mode and in an ultrasound reception mode. In the ultrasound transmission mode the ultrasound control unit 16 provides an electrical pulse to the ultrasound transducer 13, which is a piezoelectric transducer and which converts the electrical pulse to a high-frequency sound wave, i.e. to ultrasound, which propagates through the tissue wall 24 and which is reflected and/or scattered, where the tissue wall 24 is inhomogeneous. In the ultrasound reception mode the reflected and/or scattered high-frequency sound wave from the tissue wall 24 is captured using the same piezoelectric transducer, which converts it in an electrical signal, which is transmitted to the ultrasound control unit 16. In another embodiment the catheter tip 6 can also comprise several ultrasound transducers, wherein all ultrasound transducers can be adapted to send ultrasound into the tissue wall and to receive reflected and/or scattered ultrasound from the tissue wall or wherein at least one of the ultrasound transducers is adapted to send the ultrasound into the tissue wall and at least one other ultrasound transducer is adapted to receive the reflected and/or scattered ultrasound.

Figure 3:
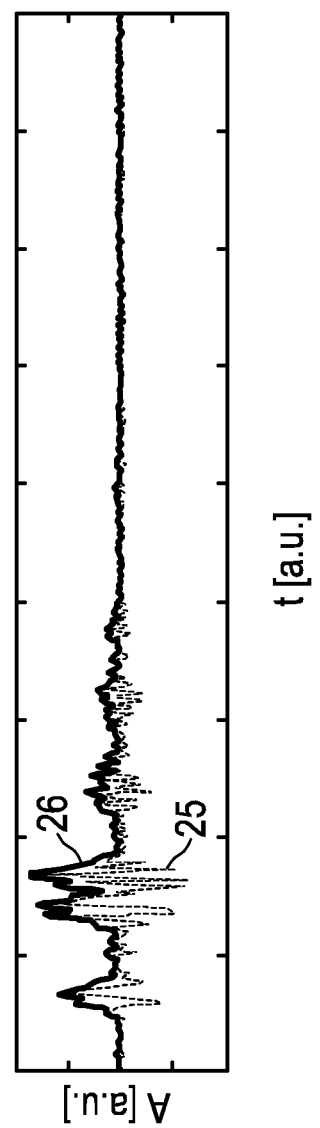
FIG. 3 shows schematically and exemplarily an A-line and an A-line envelope provided by the imaging system.

The A-lines are preferably pre-filtered by the ultrasound control unit 16 to remove noise and disturbances, thereby providing a pre-filtered A-line per transmitted ultrasound pulse. A resulting A-line 25 is schematically and exemplarily shown in FIG. 3, in which the amplitude A in arbitrary units is shown depending on the time t in arbitrary units.

The ultrasound signals providing unit 13, 16, i.e. specifically the ultrasound control unit 16, is further adapted to apply an envelope detection procedure on the A-lines and to provide the resulting A-line envelopes as the ultrasound signals. The envelope detection procedure transforms a DC-free A-line into a non-negative amplitude signal, which may also be regarded as being a non-negative intensity or contrast signal. Such an A-line envelope 26 is schematically and exemplarily shown in FIG. 3. The ultrasound control unit 16 can be adapted to apply further post-processing procedures to the A-lines like a contrast enhancement procedure for improving visualization.

The imaging system 1 further comprises a phase signal providing unit 17 for providing a phase signal being indicative of motion phases of a periodic movement of the tissue wall 24 at the different times. In this embodiment the phase signal providing unit 17 is adapted to provide a cardiac motion signal being indicative of a cardiac motion of the tissue wall 24. In another embodiment, alternatively or in addition, the phase signal providing unit can also be adapted to provide a phase signal being indicative of another kind of motion like a respiratory motion signal being indicative of respiratory motion of the tissue wall 24. The phase signal providing unit 17 is adapted to determine the phase signal from the acquired A-lines and to provide the determined phase signal.

For determining the phase signal the generated sequence of A-line envelopes can be composed to form an M-mode image, wherein subsequent M-mode image columns contain subsequent A-line envelopes. The phase signal providing unit 17 is preferentially adapted to apply a Fourier analysis or a correlation analysis in the lateral direction, i.e. in the direction of the temporal axis of the M-mode image formed by the A-line envelopes, for determining the phase signal.

Figure 4:
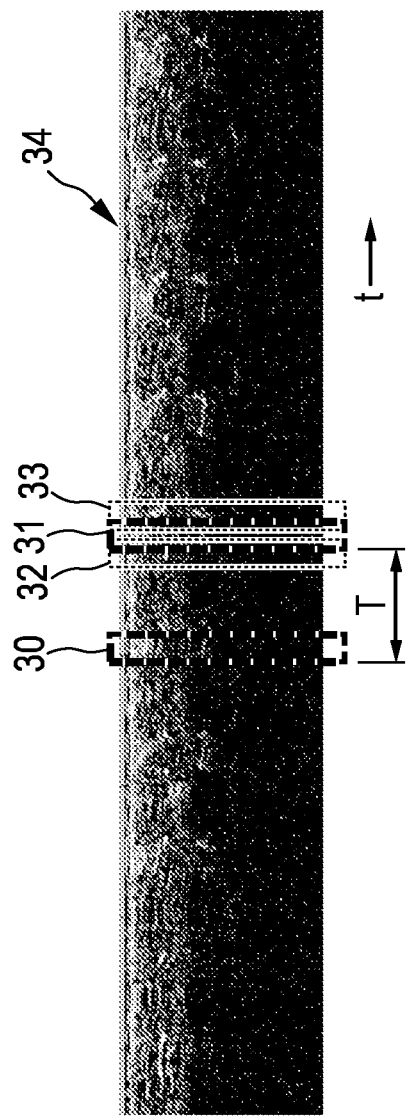
FIG. 4 shows schematically and exemplarily an ungated M-mode image for illustrating a determination of a motion period based on ultrasound image data.

FIG. 4 shows schematically and exemplarily such an M-mode image 34, wherein the lateral direction is a temporal direction indicated by t. The phase signal providing unit 17 is preferentially adapted to find the motion period T by using a signal correlation technique. Depending on the A-line sampling rate, i.e. the amount of A-lines per second, a set of consecutive A-line envelopes, which are indicated in FIG. 4 by the rectangle 30, is compared with several other sets of consecutive A-line envelopes at other times, which are indicated in FIG. 4 by the rectangles 31, 32, 33. The rectangle 31 defines the set of consecutive A-line envelopes, which is most similar to the set of A-line envelopes indicated by the rectangle 30. The temporal distance between these two sets of consecutive A-line envelopes defines the motion period T and, thus, the trigger signal, i.e. the phase signal. The comparison is based on a match error criterion, for instance, on the sum of absolute differences. The search area, i.e. the range of expected motion periods T, is preferentially defined by typical heartbeat rates and/or typical respiratory rates, if cardiac motion and/or respiratory motion, respectively, is considered. Typical heartbeat rates can be within a range of 40 to 140 beats per minute or within a range of 40 to 300 beats per minute for fibrillating atrium. The determined estimated motion period T is the period which minimizes the match error. The estimated motion period T at a time corresponds therefore preferentially to a minimal match error of two indicated sets of A-line envelopes. The trigger signal can be chosen to be non-zero only at the start of the respective new motion cycle having the duration T.

If the phase signal providing unit 17 is adapted to determine the phase signal from the ultrasound signals and to provide the determined phase signal, physical connections between different hardware systems in an electrophysiology (EP) laboratory, for instance, physical connections between an electrocardiography measurement device and a cardiac ablation monitoring device, may be reduced, in particular, avoided.

However, the phase signal providing unit can also be an electrocardiography measurement unit, wherein a cardiac trigger signal can be taken from surface leads being attached to, for instance, the breast of the person. Alternatively, the phase signal providing unit can also be adapted to take a cardiac trigger signal from an electrode inside the catheter tip, or to take the cardiac trigger signal from a conventional pulse oximeter detector that may be clipped onto a finger or an earlobe of the person. Moreover, alternatively or in addition the phase signal providing unit can also be adapted to provide a breathing trigger signal, wherein this breathing trigger signal may be taken from the airflow produced by a tracheal intubation device. The breathing trigger signal may also be extracted from a bio-impedance signal measured via electrocardiography electrodes. Moreover, the phase signal providing unit may be adapted to provide a cardiac trigger signal and/or a breathing trigger signal taken from other physiological monitoring devices, in particular from remote physiological monitoring devices.

The imaging system 1 further comprises an assigning unit 18 for assigning the ultrasound signals to the motion phases based on the provided phase signal. In particular, the determined motion period T can be subdivided into N motion phases, wherein to each A-line envelope the respective motion phase can be assigned. If, in another embodiment, the phase signal providing unit is adapted to provide an electrocardiography signal as the phase signal, the beat period, i.e. the motion period T, can be determined as defined in, for example, the article "ECG beat detection using filter banks" by V. Afonso et al., IEEE Transactions on Biomedical Engineering, volume 46, number 2, pages 192 to 202 (1999), which is herewith incorporated by reference. In particular, a heartbeat cycle, i.e. a motion period T, can be defined by the period between two subsequent R peaks of the electrocardiography signal or by any other two subsequent peaks that occur once during a heartbeat cycle. The determined heartbeat cycle, i.e. the motion period T, can be subdivided into N motion phases as schematically and exemplarily shown in FIG. 5.

Figure 5:
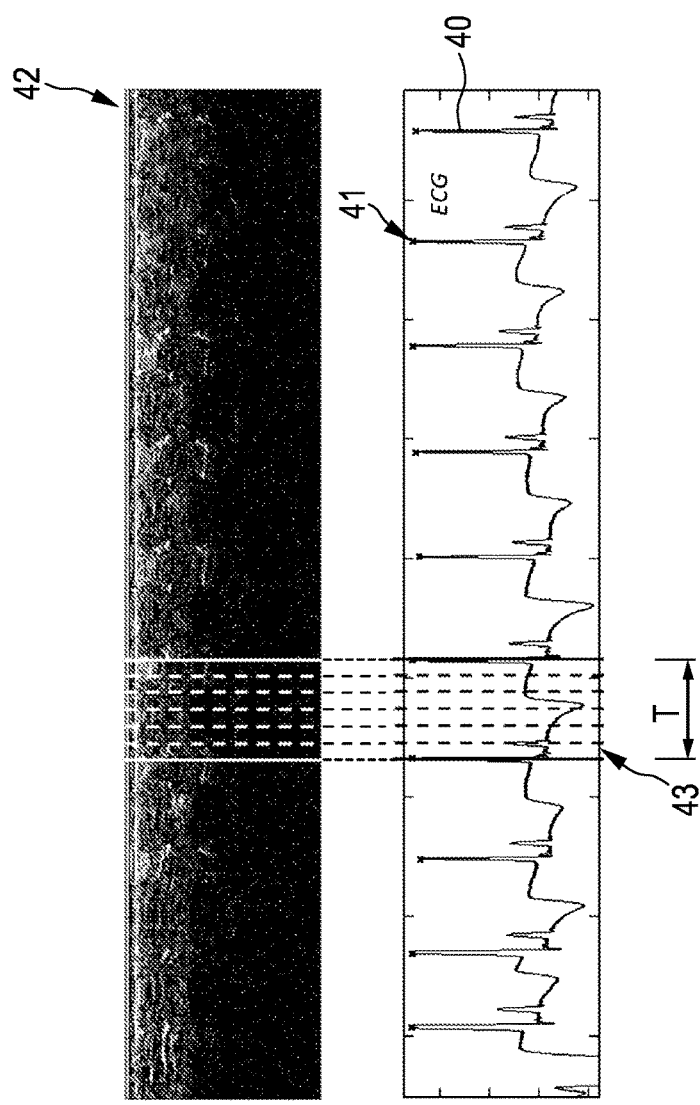
FIG. 5 shows exemplarily and schematically a cardiac phase signal and an ungated M-mode image for illustrating an assignment of A-lines to motion phases.

In FIG. 5 the upper part shows temporally consecutively the A-line envelopes, which form an M-mode image 42, and the lower part shows the provided phase signal being, in this example, an electrocardiography signal 40. The R peaks of the electrocardiography signal 40 are indicated by crosses 41. For one motion period T the subdivision into N phases is indicated. All A-line envelopes within, for instance, the region indicated in FIG. 5 by reference number 43 are assigned to the same motion phase, i.e. in this embodiment to the first motion phase. The further A-line envelopes of the period T are assigned to the respective further motion phases.

Figure 6:
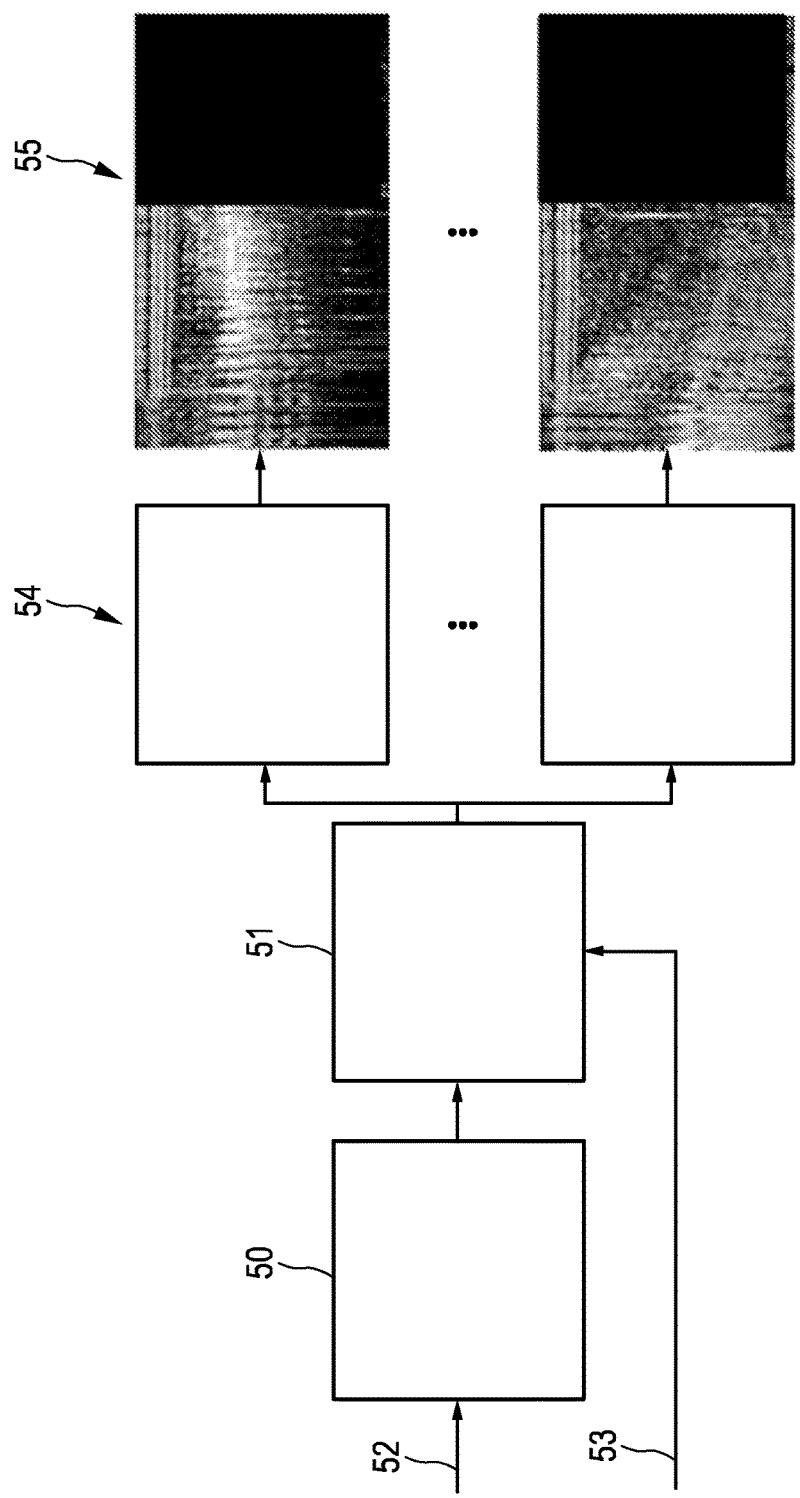
FIG. 6 shows a flowchart exemplarily illustrating a generation of gated M-mode images.

The imaging system 1 further comprises an ultrasound images generation unit 19 for generating several ultrasound images for the different motion phases, wherein an ultrasound image for a motion phase is generated based on the ultrasound signals assigned to the respective motion phase. In this embodiment the ultrasound images generation unit 19 is adapted to generate for each motion phase an M-mode image, wherein an M-mode image for a motion phase is generated from the A-line envelopes assigned to the respective motion phase. The generation of the several M-mode images can be regarded as being an extraction of N gated ultrasound images from an original M-mode image which is composed of all non-gated A-line envelopes, wherein the extraction is triggered by the phase signal being synchronous with the heart beating and optionally breathing motion. In other embodiments the phase signal can also be synchronous with the breathing motion only. In each gated ultrasound image groups of subsequent A-line envelopes are collected that belong to one particular motion phase of the motion cycle. Consequently, from one gated ultrasound image being formed over time by appending the A-line envelopes having been assigned to the respective motion phase changes inside the tissue wall can be observed, which may be caused by ablation, wherein motion artifacts are reduced in the respective gated ultrasound image or are not present at all. The generation of the gated M-mode images, while the A-line envelope data are generated, will exemplarily be described with reference to FIG. 6 in the following.

Raw ultrasound A-line data, which are generated by the ultrasound transducer 13, are received (52), wherein the received raw ultrasound A-line data are processed for generating filtered A-line envelope data (50). The A-line envelopes are assigned to the different motion phases (51) based on a received trigger signal (53). The A-line envelopes, which have been assigned to the different motion phases, are then appended to the respective M-mode image of the respective motion phase (54), which results in N updated M-mode images (55). Thus, for each motion phase corresponding A-line envelopes are extracted from an original M-mode image and placed behind previously extracted A-line envelopes of the same motion phase of a previous motion period. In this way an M-Mode image is subdivided into N gated images, wherein each gated image corresponds to one particular motion phase of the motion cycle.

Since the accurate division of a motion period in frames, i.e. in motion phases, which can vary in duration between motion periods, for instance, due to variations in heart rate, can only be performed after the respective motion period has finished, the generation and displaying of a gated ultrasound image may be performed with a relatively large latency. The assigning unit 18 is therefore preferentially adapted to split a motion period into motion phases based on the duration of the previous motion period and to compensate/correct for potential errors due to a potential difference in duration between subsequent motion periods after the actual motion period has been finished. The ultrasound images generation unit 19 is then preferentially adapted to correct the gated ultrasound images based on the corrected assignments of the A-lines to the motion phases, in particular, by generating the gated ultrasound images again based on the corrected assignments. This may allow for a generation and displaying of a gated ultrasound image with very low latency.

Referring again to FIG. 2, the catheter tip 6 further comprises an energy application unit 12 being, in this embodiment, an RF ablation electrode for applying energy to the tissue wall 24. The catheter 5 forms therefore a sensing probe, in which the ultrasound transducer 13 and the RF ablation electrode 12 are integrated. The RF ablation electrode 12 is connected with an RF source 22 via an electrical connection 14 like an insulated wire.

The imaging system 1 further comprises a selecting unit 20 for selecting an ultrasound image from the generated ultrasound images. In particular, the selecting unit 20 is adapted to select one or several gated M-mode images from the generated gated M-mode images provided by the ultrasound images generation unit 19. The selecting unit 20 can be adapted to allow a user to select a gated ultrasound image from the generated gated ultrasound images and/or to automatically select a gated ultrasound image from the generated gated ultrasound images. For instance, the selecting unit 20 can be adapted to provide a graphical user interface 60, which is schematically and exemplarily shown in FIG. 7.

The graphical user interface 60 shows in the lower part a row 63 of ten generated gated ultrasound images, i.e. in this example it is assumed that the motion period has been subdivided into ten motion phases. However, the respective motion period can of course also be subdivided into another number of motion phases. In particular, the selecting unit 20 can be adapted to allow a user to manually set a desired number of motion phases per motion period. For instance, the selecting unit 20 can comprise a graphical user interface allowing a physician to manually set the number of motion phases to be between one and twenty. The selected gated ultrasound image can be highlighted within the row 63. For example, the selected gated ultrasound image can be provided with a frame 64 for highlighting the same. The selected gated ultrasound image 61 is shown with a larger size by the graphical user interface 60. Also the gated ultrasound image 61 shown with larger size can be highlighted by being provided with a frame 62. The graphical user interface 60 is shown on a display unit 21. For manually selecting the gated ultrasound image, the selecting unit 20 may be adapted to allow a user to select the respective gated ultrasound image by using, for instance, a computer mouse pointer or a touch sensitive display.

Figure 7:
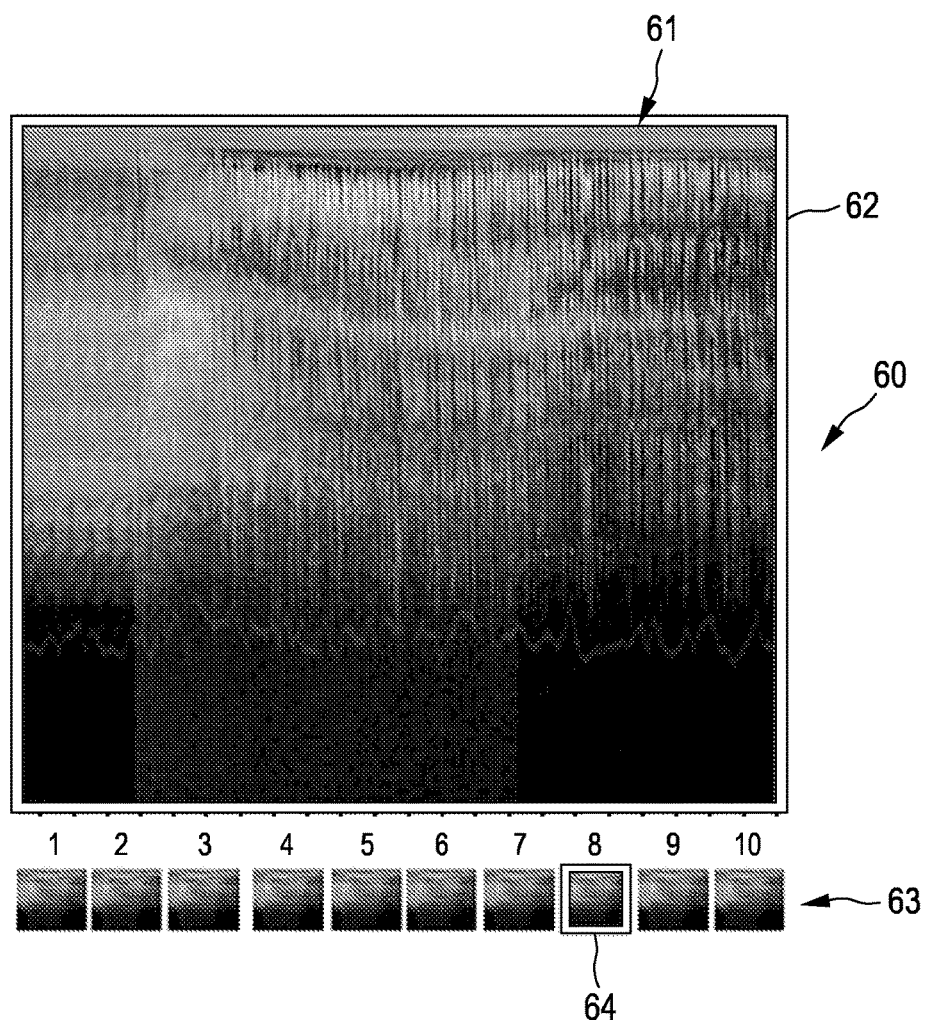
FIG. 7 shows schematically and exemplarily an embodiment of a graphical user interface showing a selected gated M-mode image.

Although the graphical user interface 60 exemplarily and schematically in FIG. 7 also shows the non-selected gated ultrasound images in the row 63, in another embodiment the display unit 21 may only show the respective selected gated ultrasound image.

For automatically selecting one or several gated ultrasound images, the selecting unit 20 is preferentially adapted to determine selection values for the generated gated ultrasound images, wherein a selection value is determined based on the image values of the respective gated ultrasound image, and to apply selection rules to the selection values for selecting a gated ultrasound image from the generated gated ultrasound images. Preferentially, the selecting unit 20 is adapted to determine at least one of the following selection values for each of the gated ultrasound images: a first distance value being indicative of a distance between the sensing probe, i.e. the catheter tip 6, and an outer surface 28 of the tissue wall 24, a wall thickness value being indicative of a thickness of the tissue wall 24, a transmurality value being indicative of a part of the tissue wall 24 being influenced by the application of energy, a second distance value being indicative of a distance between an outer surface 29 of the tissue wall 24 and further tissue, which may be present in a region 39 behind the tissue wall 24, and a gas formation value being indicative of an amount of gas formed in the tissue wall 24. The transmurality value can be defined as being the ratio between i) the distance of the boundary of a lesion, which has been created by the ablation procedure, to the outer surface 28 of the tissue wall 24 and ii) the wall thickness value. In other words, the transmurality value is preferentially the ratio between the ablation depth and the thickness of the tissue wall 24.

The selection values may be different for different gated ultrasound images because of the periodic movement of the tissue wall 24. This and advantages of displaying the selected image instead of displaying an ungated M-mode image will in the following exemplarily be described with reference to FIGS. 8 to 11.

Figure 8:
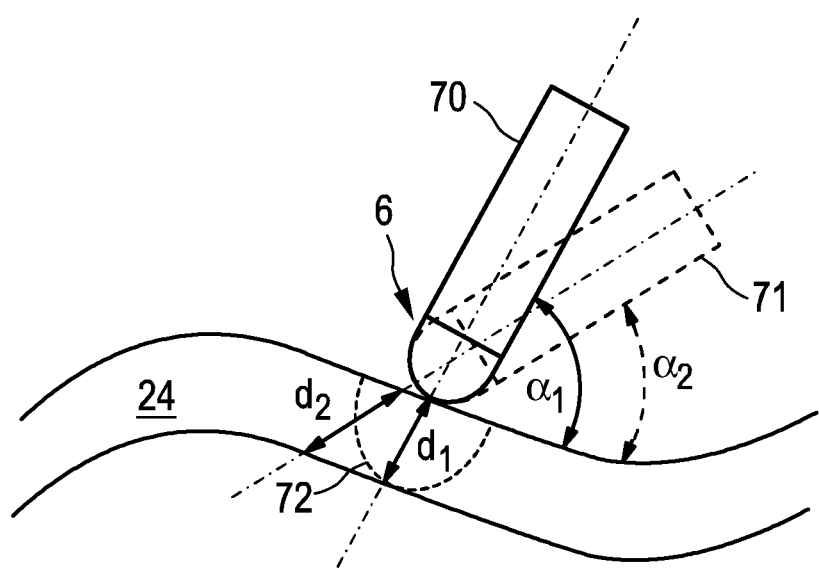
FIGS. 8 to 11 illustrate different kinds of disturbances of ultrasound imaging caused by periodic cardiac and respiratory movements.

FIG. 8 shows the tip 6 of the catheter 5 in two different positions 70, 71, which correspond to two different angles $\alpha_1$, $\alpha_2$, which the catheter tip 6 encloses with the outer surface of the tissue wall 24. Because of the periodic motion of the tissue wall 24 the catheter tip 6 periodically changes between the different positions 70, 71 with respect to the outer surface of the tissue wall 24. As it is clear from FIG. 8, if the thickness $d_1$ of the tissue wall 24 is determined based on a gated ultrasound image, which corresponds to a motion phase in which the catheter tip 6 is in the first position 70, and if a second thickness $d_2$ of the tissue wall 24 is determined based on a gated ultrasound image, which corresponds to a motion phase in which the catheter tip 6 is in the second position 71, the two determined thicknesses $d_1$, $d_2$ are different. Thus, wall thickness values, which have been determined for different gated ultrasound images, can be different. Correspondingly, also the lesion formation, which is indicated in FIG. 8 by the broken line 72, can be seen to be "deeper" or "less deep" depending on the respective position 70, 71 of the catheter tip 6. Also the transmurality value can therefore be different for different gated ultrasound images.

These effects lead to the fact that in a known ungated M-mode image the thickness variation, which may be very rapid, is hard to interpret by a physician and that the physician may judge the thickness to be $d_2$, while in real it is $d_1$. Thus, if the physician would perform the ablation procedure based on a known ungated M-mode image, the physician may choose a too aggressive ablation regime. Moreover, if the physician monitors the ablation procedure based on a known ungated M-mode image, the physician may miss the first transmural point such that the ablation may become ineffective and too long, thereby potentially damaging adjacent tissue.

Figure 9:
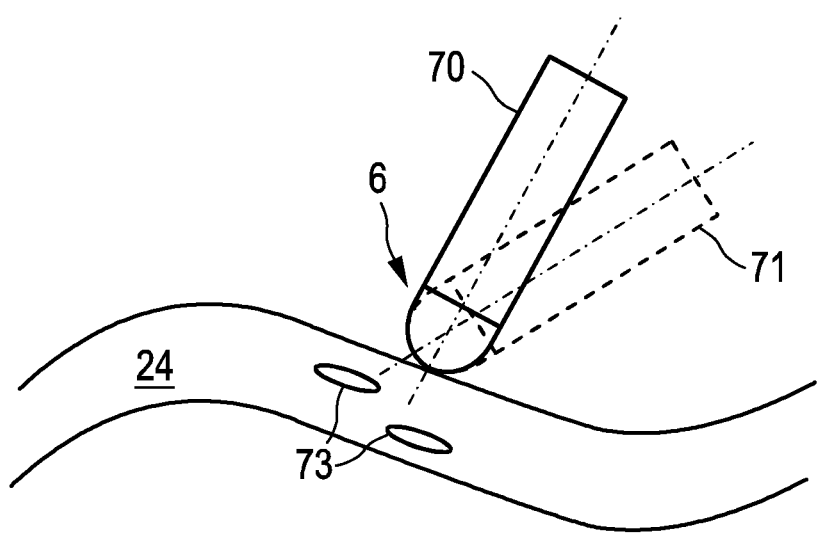

FIG. 9 shows different tissue structure elements 73, which may move in and out of the ultrasound beam provided by the ultrasound transducer 13. In a known ungated M-mode image this in and out moving of the tissue structure elements 73 would disturb the M-mode image and therefore reduce the visibility of lesion formation. Furthermore, since the tissue structure elements 73 contribute to the different gated ultrasound images differently, they may differently influence the determination of the selection values in the different gated ultrasound images.

Figure 10:
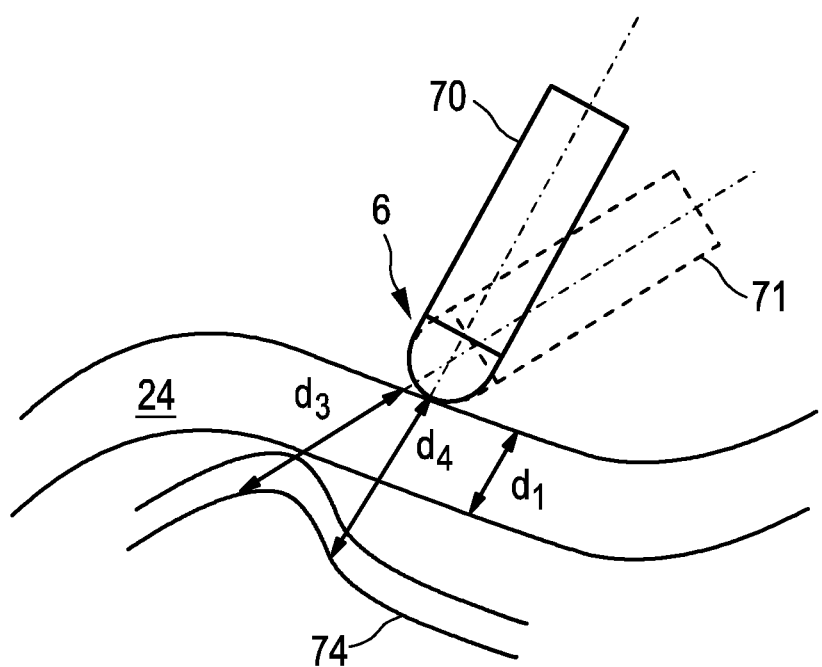

In FIG. 10 a second tissue layer 74 like pericardial sac, lung tissue or a fat layer is shown behind the tissue wall 24. In a known ungated M-mode image the second tissue layer 74 and the tissue wall 24 may not be separable, because the motion of the tissue wall 24 and the second tissue layer 74 mixes these two elements in the known ungated M-mode image. For instance, in the example shown in FIG. 10 the distance $d_3$ is equal to the distance $d_4$, wherein the tissue gap along $d_4$, which will be shown as a dark region in the M-mode image, is hard to observe, because a bit later in time, when the catheter tip 6 is positioned along $d_3$, a tissue gap does not exist and the corresponding region in the gap M-mode image shows up bright. In a known ungated M-mode image, which covers the long required period of time to see lesion progression of, for instance, 60 seconds, the individual A-lines are plotted so close together that the tissue gaps along $d_4$ cannot be observed. Thus although the actual tissue layer thickness, i.e. the thickness of the tissue wall 24, is $d_1$, the physician may believe that the thickness is equal to $d_3$. Moreover, a second distance value being indicative of a distance between the tissue wall 24 and the second tissue layer 74 and which is determined for a gated ultrasound image, which corresponds to a motion phase in which the catheter tip 6 is in the first position 70, will be different to a second distance value, which is determined for a gated ultrasound image, which corresponds to a motion phase in which the catheter tip 6 is in the second position 71.

Figure 11:
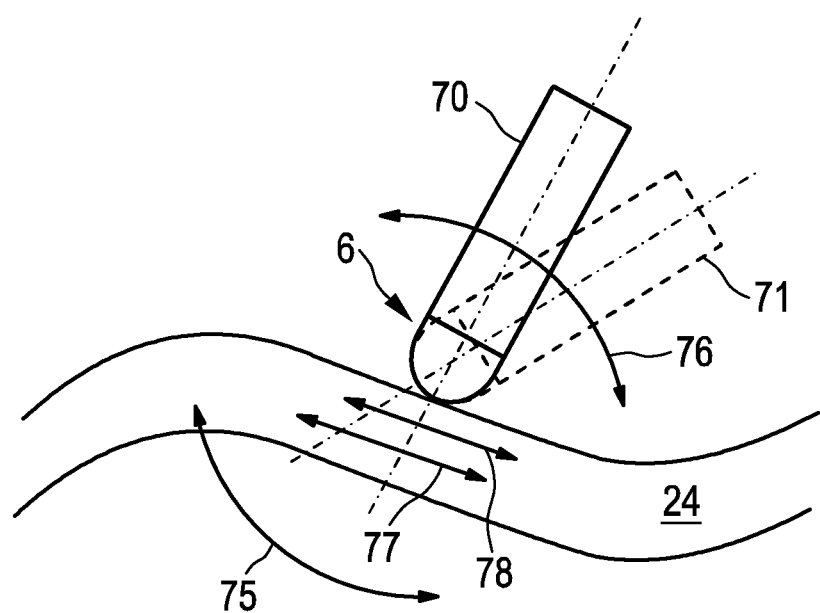

In FIG. 11 motion caused by heart beating and breathing is indicated by arrows 75, 76 and motion caused by locally contracting tissue is indicated by arrows 77, 78. In a known ungated M-mode image contrast variations in the M-mode image due to the heart beating and breathing motion may interfere with contrast variations due to local muscle contraction. Because of this interference the local muscle contractions cannot be observed in the ungated M-mode image, although their magnitude difference before and after ablation can be an important indicator of the level of necrosis, in other words an important indicator of how well the ablation procedure went. Moreover, the heart beating and breathing motion and the motion due to local muscle contraction can lead to different selection values determined for different gated ultrasound images.

It is assumed that at least one of the N-gated ultrasound images is better than the other gated ultrasound images for the visualization of an aspect. For example, one of the N-gated images may be associated with the minimum observed wall thickness of the heart, which is expectedly the actual wall thickness. Such a gated ultrasound image may be the gated ultrasound image, which corresponds to the first position 70 shown in FIG. 8. The imaging system is therefore preferentially adapted to replace the conventional ungated M-mode image by one or several gated M-mode images for displaying such that the respective relevant aspect is displayed optimally.

The choice of a particular gated ultrasound image to be displayed can be made by a physician. The physician can select one or several gated ultrasound images from all the gated ultrasound images, which may all be shown simultaneously, in particular with a relatively low resolution to fit on the display unit 21. The choice of the physician may be based on his/her own experience. After the selection has been made, the chosen gated ultrasound image is preferentially displayed with a best possible resolution by the display unit 21.

As an alternative to allowing a user to select a desired gated ultrasound image, the selecting unit 20 can be adapted to automatically select a gated ultrasound image to be visualized by using an algorithm. In particular, firstly each gated ultrasound image is automatically analyzed by the algorithm to estimate one or multiple relevant aspects like the tissue thickness, the lesion depth, the amount of gas formation, et cetera, i.e. to determine the selection values.

Figure 12:
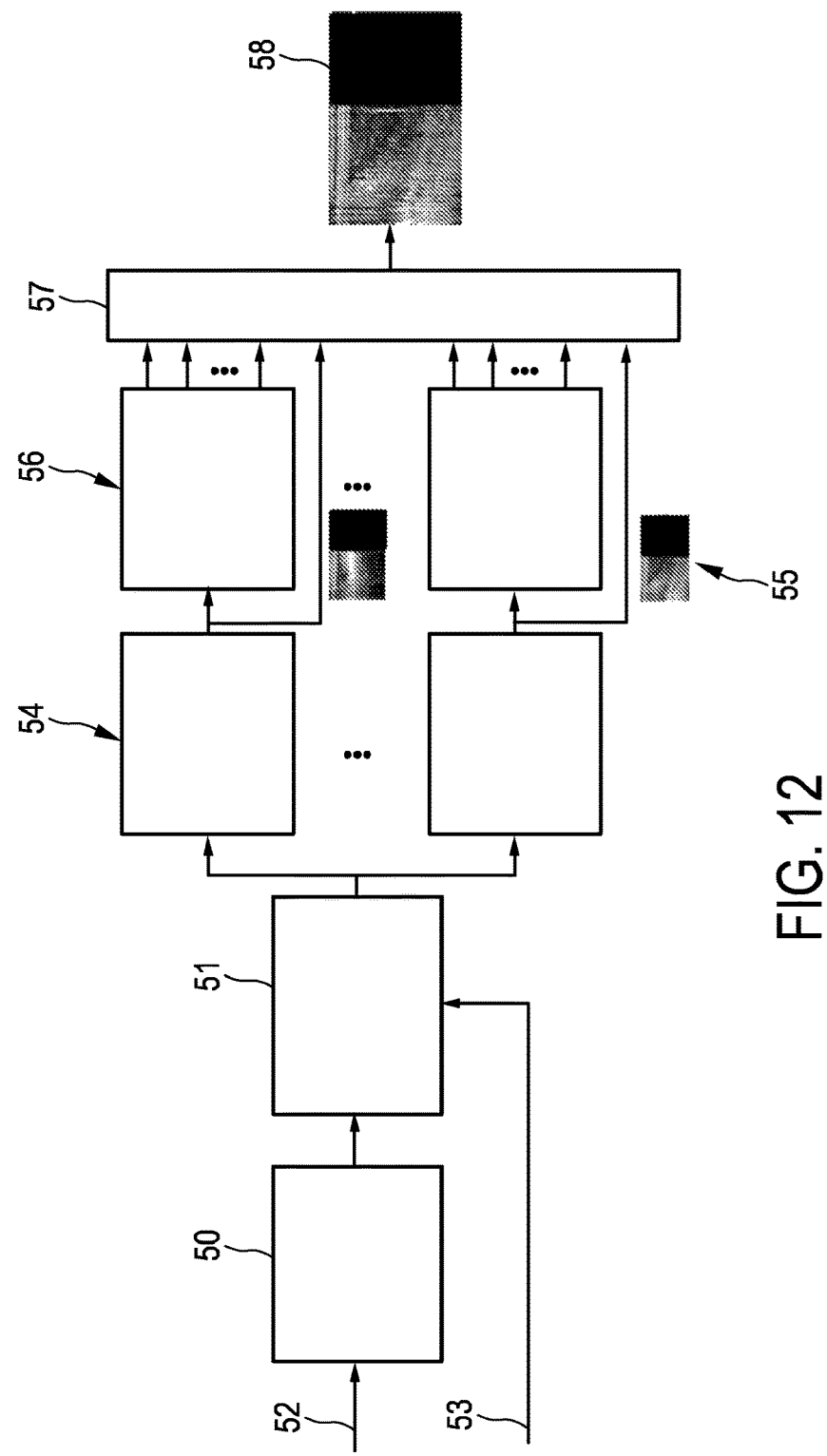
FIG. 12 shows a flowchart exemplarily illustrating a generation, selection and displaying of one or several gated M-mode images.

Then, the best gated ultrasound image for displaying is selected automatically on the basis of at least one estimated image aspect, i.e. on the basis of at least one of the determined selection values. The process of generating several gated ultrasound images and of selecting one of the gated ultrasound images for displaying the same will in the following be exemplarily described with reference to FIG. 12.

After the N gated ultrasound images 55 have been generated as described above with reference to FIG. 6, the selecting unit 20 analyzes each gated ultrasound image for determining for each gated ultrasound image at least one selection value (56). The selecting unit 20 then selects one or several of the gated ultrasound images 58 based on the determined selection values and predefined selection rules (57). The selected one or several gated ultrasound images 58 are then shown on the display unit 21.

As explained above with reference to FIG. 8, the observed tissue thickness depends on an interfacing angle between the catheter tip 6 and an outer surface of the tissue wall 24. The true tissue thickness, i.e. the true thickness of the tissue wall 24, is equal to the minimum observed tissue thickness across the different gated ultrasound images. Thus, the selecting unit 20 can be adapted to select that gated ultrasound image for displaying that yields the minimum observed tissue thickness. Alternatively or in addition, the selecting unit 20 can be adapted to select from all gated ultrasound images that one which has the best tissue contact, for instance, for which the smallest first distance value has been determined.

For determining the thickness of the tissue wall 24, i.e. for determining the wall thickness value, the selecting unit 20 can be adapted to process the A-line data as follows. Along an A-line it can be searched for the point, where the ultrasound reflected signal is below a noise threshold. More specifically, the A-line data can be analyzed in the spectrum domain by subdividing an A-line into segments, wherein neighboring segments may overlap. Each segment is Hamming-windowed before a fast Fourier transformation is applied. Then, by squaring the resulting complex-valued numbers a power spectrum is achieved for each segment of the A-line. Optionally, power spectra of several corresponding segments of subsequent A-lines can be averaged, in order to reduce noise. The combination of the different power spectra of the different segments of an A-line provides a spectrogram being a two-dimensional array of data which depend on the frequency and an A-line segment depth. Since only a frequency band around the resonance frequency of the ultrasound transducer 13 is relevant here, the following processing is only applied to this frequency band. A total energy number E and a normalized variance number V between 0 and 1 around the resonance frequency is computed per segment along the A-line. A small variance number in combination with a sufficiently large total energy number implies the presence of a narrow-band signal, thus the presence of a response from the transmitted ultrasound pulse. The selecting unit 20 can therefore be adapted to conclude that for a given A-line segment an ultrasound reflection signal is present, if following inequality condition is met:

$$E \cdot (1-V) > \theta. \tag{1}$$

In equation (1), $\theta$ is a number representative of the expected noise level. The first segment along the A-line, where the ultrasound reflection signal is present, corresponds to the beginning of the tissue wall and the next segment along the A-line, where the ultrasound reflection signal is not longer present, corresponds to the end of the tissue wall. The expected noise level $\theta$ can be determined by calibration or training measurements.

Alternatively, the selecting unit 20 can be adapted to apply a texture classification technique to a respective gated M-mode image for determining the thickness of the tissue wall. This technique provides a classification output per pixel of the respective gated M-mode image or per region of pixels of the respective gated M-mode image, wherein the texture classification technique can be trained to find tissue in the respective gated M-mode image. The texture classification technique can be a texture based feature detection technique to be applied on the so-called gray level co-occurrence matrix (GLCM), which is well-known in the field of medical signal processing and which is disclosed, for instance, in the article "Texture based feature extraction: application to burn scar detection in Earth observation satellite sensor imagery" by A. M. S. Smith et al., International Journal of Remote Sensing, volume 23, number 8, pages 1733 to 1739 (2002), which is herewith incorporated by reference. Thus, the respective gated M-mode image can be subdivided into potentially overlapping rectangular image regions of varying sizes to accommodate image textures at various scales. Per image region the GLCM is computed and from the GLCM a set of texture features is derived. With these features and with annotated reference M-mode data a machine learning technique like Adaboost, which is disclosed in the article "A decision-theoretic generalization of on-line learning and an application to boosting" by Y. Freund et al., Journal of Computer and System Sciences, volume 55, pages 119 to 139 (1997), is preferentially used to train the texture classification for finding the tissue, in particular for finding heart tissue. After the texture classifier has been trained, the selecting unit 20 can determine for each image region the GLCM and from the GLCM for each image region texture features, which can then be input to the trained texture classifier for finding image regions within the respective gated M-mode image, which show tissue. After it has been determined, which image regions show tissue and which image regions do not show tissue, the thickness of the tissue wall 24 and also the distance of the catheter tip 6 to the outer surface 28 of the tissue wall 24 can be determined by the selecting unit 20.

The selecting unit 20 is preferentially further adapted to determine the transmurality level, i.e. determine the transmurality value, as the ratio between an observed depth of a lesion boundary, which is marked by the broken line 72 in FIG. 8, and the observed tissue thickness as determined by the selecting unit 20. For determining the lesion boundary 72 the selecting unit 20 can be adapted to analyze tissue elasticity from a correlation or strain analysis between consecutive A-lines. In particular, lesion tissue has a lower elasticity than healthy tissue such that the selecting unit 20 can be adapted to determine an elasticity transition between consecutive A-lines for determining the lesion boundary.

Since the determined transmurality value may be different for different gated ultrasound images and since it is assumed that the actual transmurality level is defined by the ratio between the minimum observed tissue thickness and the maximum observed lesion boundary depth, which will normally occur in the same gated ultrasound image for geometrical reasons, i.e. since the gated ultrasound image, for which the corresponding largest transmurality value has been determined, is regarded as showing most likely the real actual transmurality level, the selecting unit 20 may be adapted to select this gated ultrasound image for displaying.

Adjacent tissue structures like the tissue wall 24 and the second tissue layer 74 shown in FIG. 10 move towards and away from each other. The selecting unit 20 can be adapted to select that particular gated ultrasound image for displaying that corresponds to the maximum distance between the different adjacent tissue structures, for example, between heart tissue and lung tissue, in order to maximally make clear the distinction between the two kinds of tissue. Alternatively, the selecting unit 20 may be adapted to select the gated ultrasound image that shows a minimum distance between the different tissue layers, in order to show as good as possible how close the lesion is progressing towards the adjacent tissue, in particular towards lung tissue. Thus, the selecting unit 20 can be adapted to select the gated ultrasound image, for which the largest second distance value or the smallest second distance value has been determined. For determining the second distance value the selecting unit 20 can be adapted to use the above described methods, which are also used for determining the tissue thickness and which can also be used for determining the distance between the catheter tip 6 and the outer surface 28 of the tissue wall 24, i.e. the selecting unit 20 can be adapted to use the above described comparison with a noise threshold level or the above described texture classification technique for determining the second distance value.

In some cases there can be gas formation inside the tissue wall, in particular inside the heart wall. The ablation procedure should be stopped as soon as possible, when gas is being formed, in order to prevent a tissue pop. It is therefore preferred to display to a physician, who performs an ablation procedure, that particular gated ultrasound image that shows the largest gas formation cloud in the image. The selecting unit 20 can therefore be adapted to determine for each gated ultrasound image the size, i.e., for example, the amount of image pixels, of a gas cloud, when it occurs, and to select the gated ultrasound image for displaying that shows the largest gas cloud, while the tissue wall 24 is ablated. For determining the corresponding gas formation value the selecting unit 20 is preferentially adapted to use the above described texture classifier, which may be based on a GLCM, in order to find image regions in the respective gated ultrasound image, which show gas formation. The gas formation value can then be determined by counting all pixels or pixel regions, in which gas is being formed.

The selecting unit 20 is preferentially adapted to follow a dynamic selection strategy for the gated ultrasound image, implying that at different times when different selection aspects are of highest performance a different gated ultrasound image is displayed. In particular, the ablation of the tissue wall 24 can be performed in accordance with an energy application procedure having different stages, wherein the selecting unit 20 is preferentially adapted such that the selection rules define the selection of a gated ultrasound image depending on the determined selection values and depending on the respective stage of the energy application procedure. In particular, the selection rules preferentially define that in a first stage before applying energy to the object firstly a gated ultrasound image is selected, for which an average first distance value has been determined, and secondly a gated ultrasound image is selected, for which the smallest wall thickness value has been determined.

Prior to the start of ablation, i.e. in the first stage, it is mostly important for the physician to verify a good catheter-tissue contact and to know the heart tissue thickness. If the catheter-tissue contact is intermittent, i.e. only touching at some moments because of the motion, the physician should apply slightly more force to the catheter tip 6. Generally, the display unit 21 could show that particular gated ultrasound image that belongs to the largest distance between the catheter tip 6 and the outer surface 28 of the tissue wall 24, i.e. that belongs to the largest first distance value. However, this may lead the physician to applying a too large force. For this reason it is preferred that the selecting unit 20 selects the particular gated ultrasound image that corresponds to the average distance value. Displaying the gated ultrasound image, for which the average first distance value has been determined, will guide the physician to not apply too much force to the catheter.

If proper tissue contact has been achieved, still prior to the start of the application of energy, i.e. still prior to the start of the ablation in the first stage, that particular gated ultrasound image is preferentially selected for displaying that resulted in the smallest observed tissue thickness value, i.e. for which the smallest wall thickness value has been determined. This allows a physician to optimally set the ablation regime, for instance, to optimally set the power amplitude and power duration to be applied. If in an embodiment the catheter also provides cooling functionality by providing a cooling fluid for cooling the catheter tip, in particular the ablation electrode 12, the physician can also optimally set the cooling flow rate depending on the shown thickness of the tissue wall.

The selecting unit 20 is preferentially further adapted such that the selection rules define that in a second stage during applying energy to the tissue wall 24 an ultrasound image, for which the largest transmurality value has been determined, and, in addition or alternatively if gas formation occurs, an ultrasound image, for which the largest gas formation value has been determined, are selected.

As soon as ablation starts the level of reached transmurality becomes the most important aspect and the selected gated ultrasound image is therefore the one showing the highest transmurality ratio, which overrules the decision taken upon tissue contact and tissue thickness. If several gated ultrasound images show equal highest transmurality ratios, i.e. if for several gated ultrasound images the same highest transmurality value has been determined, the selecting unit 20 is preferentially adapted to select from these gated ultrasound images the one that shows the largest separation between an adjacent tissue structure and the first tissue structure, i.e. the tissue wall 24. Thus, in this case from the gated ultrasound images, for which the same highest transmurality value has been determined, the gated ultrasound image is selected, for which the largest second distance value has been determined. This allows the physician to monitor the transmurality of the tissue wall and to stop the ablation in time such that the adjacent structure is not damaged in an optimal way. The second tissue structure is, for instance, esophagus, lung tissue, secondary cardiac tissue like tissue from the atrium towards the ventricle et cetera.

If during ablation gas formation is observed, the level of gas formation becomes the most important aspect for the selection of the gated ultrasound image such that the gated ultrasound image showing the largest gas value, i.e. for which the largest gas formation value has been determined, is selected for displaying. This selected gated ultrasound image showing the largest gas cloud is shown alone or together with the gated ultrasound image, for which the largest transmurality value has been determined.

The selecting unit 20 is preferentially further adapted such that the selection rules define that in the third stage after applying energy to the tissue wall 24 a gated ultrasound image is selected, for which the largest transmurality value has been determined.

A position detection system 7 can be used to detect the position of the tip 6 of the catheter 5 within the person 2. In this embodiment the position detection system 7 is an x-ray fluoroscopy system, in particular, an x-ray C-arm system. The x-ray fluoroscopy system comprises an x-ray source 8 for generating x-rays 9 which traverse the person 2 on the table 3, wherein the x-rays 9, which have traversed the person 2, are detected by an x-ray detector 10. The x-ray fluoroscopy system 7 further comprises a fluoroscopy control unit 11 for controlling the x-ray source 8 and the x-ray detector 10. The x-ray detector 10 generates x-ray images of the person 2, which can be shown on the display unit 21. On the generated x-ray images the tip 6 of the catheter 5 is visible within the person 2 such that the x-ray images show the position of the tip 6 of the catheter 5 within the person 2. In other embodiments other position detection systems for detecting the position of the catheter tip within the person can be used like position detection systems which are based on electromagnetic sensors, ultrasound sensors, et cetera.

The imaging system 1 further comprises a navigation unit 23 for allowing the catheter 5, in particular, the catheter tip 6, to be navigated to a desired location within the person 2. The navigation unit 23 can be adapted to allow a user to navigate the catheter 5 completely by hand or semi-automatically. The catheter 5 comprises built-in guiding means (not shown in FIG. 1), which can be controlled by the navigation unit 23. The catheter 5 can, for example, be steered and navigated by the use of steering wires, in order to guide the catheter tip 6 to a desired location within the person 2.

Figure 13:
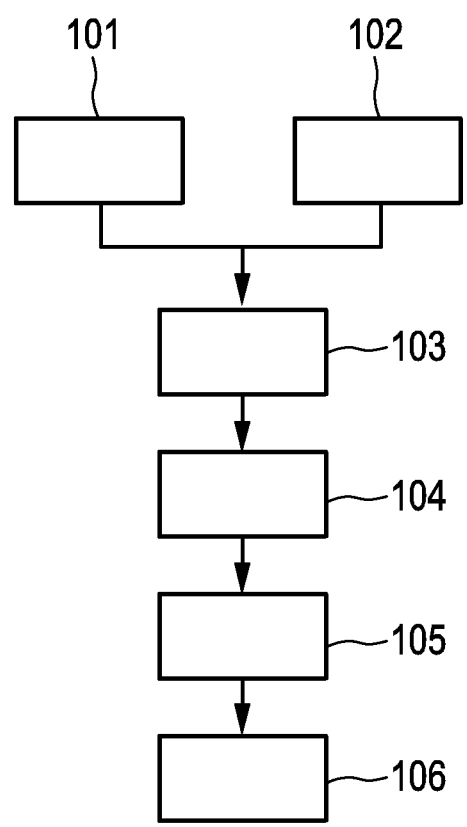
FIG. 13 shows a flowchart exemplarily illustrating an embodiment of an imaging method for imaging a periodically moving object.

In the following an embodiment of an imaging method for imaging a periodically moving object will exemplarily be described with reference to a flowchart shown in FIG. 13.

In step 101 ultrasound signals of the object are provided for different times by an ultrasound signals providing unit. In particular, the ultrasound signals providing unit acquires A-lines, pre-filters the A-lines for removing noise and applies an envelope detection algorithm on the pre-filtered A-lines for generating A-line envelopes as the ultrasound signals. In step 102 a phase signal being indicative of motion phases of a periodic movement of the object at the different times is provided by a phase signal providing unit. For instance, a cardiac signal being indicative of a cardiac motion of the object at the different times, for which the A-lines have been provided, is provided as the phase signal. In step 103 the ultrasound signals are assigned to the motion phases based on the provided phase signal by an assigning unit. Preferentially, the provided A-line envelopes are assigned to different cardiac phases based on the cardiac signal. In step 104 several ultrasound images are generated for the different motion phases by an ultrasound images generation unit, wherein an ultrasound image for a motion phase is generated based on the ultrasound signals assigned to the respective motion phase. For instance, each A-line envelope, which has been assigned to a certain motion phase, is used for generating an M-mode image for this certain motion phase. Thus, if a new A-line envelope has been provided and assigned to a certain motion phase, this A-line envelope can be appended to the respective M-mode image of the respective motion phase. In step 105 from the generated ultrasound images one or several ultrasound images are selected by a selecting unit. For instance, a person like a physician can use the selecting unit for selecting a desired ultrasound image or the selecting unit can automatically select one or several ultrasound images. In step 106 the one or several selected ultrasound images are displayed on a display unit.

Steps 101 to 106 can be performed continuously such that continuously ultrasound signals, in particular A-lines, are generated, assigned to the respective motion phase and appended to the respective M-mode image for continuously updating the M-mode images, which are generated for the different motion phases, and such that the selection procedure is continuously applied to the continuously updated M-mode images and the currently selected one or several selected updated M-mode images are displayed. Because of this continuous process different gated M-modes images, which correspond to different motion phases, may be displayed temporally consecutively by applying the same selection rules.

The imaging system preferentially comprises an ultrasound transducer mounted inside a catheter for ultrasound imaging inside a body of a person. The imaging system is preferentially adapted to monitor cardiac ablation, which is preferentially performed for curing certain arrhythmia. The imaging system therefore preferentially comprises a catheter with an ablation electrode and an ultrasound transducer in its tip, in order to enable a physician in an EP laboratory to assess almost in realtime certain relevant parameters of a heart wall from the inside. By visual inspection of a selected gated M-mode image the physician may measure the heart wall thickness and decide on the best ablation regime, i.e. the physician may set the ablation power, the flow rate of fluid cooling and the ablation duration based on the heart wall thickness shown on the displayed M-mode image. Moreover, the physician can monitor the lesion formation while ablating and halt the ablation when a lesion has become transmural, i.e. when the treatment has reached the backside of the heart wall. In case steam pocket is formed inside the heart tissue, the physician can see this on the displayed M-mode image and can halt the ablation, in order to prevent tissue rupture, i.e. a so-called "pop".

The displayed M-mode image comprises subsequent M-mode image columns which preferentially contain subsequent A-line envelopes up until the current time instance. When time progresses, the displayed M-mode image is extending to the right, replacing one black image column with one newly acquired A-line envelope, which has been assigned to the motion phase of the displayed M-mode image, at a time. After the end of the display has been reached, the new A-line envelope is plotted on the first display column replacing the oldest displayed A-line envelope from the history, and so forth.

A conventional non-gated M-mode image would show distorting artifacts that originate from the motion due to tissue-catheter interaction during heart beating and/or breathing, which causes the field-of-view of the ultrasound transducer to change and the A-line data to correspond to different parts of the tissue. Such distortion artifacts inhibit a good and rapid interpretation of the ungated M-mode image data by the physician. In order to overcome these drawbacks of a conventional ungated M-mode image, the imaging system is adapted to display one or several selected gated M-mode images, wherein the choice of the particular gated one or several ultrasound images from all created gated ultrasound images can be made by the physician via the selecting unit, which can provide a corresponding graphical user interface for selecting one or several desired gated ultrasound images, on the basis of the physician's judgement from visual inspection, or one or several particular gated ultrasound images can be selected automatically by the selecting unit. In particular, the selecting unit can be adapted to use an algorithm that automatically interprets the data. Such interpretation algorithm can adapted to select one gated ultrasound image from all gated ultrasound images on the basis of one or more aspects such as an estimated, i.e. determined, distance between a catheter tip and tissue, or an estimated value of the pre-ablation wall thickness, or an estimated transmurality level, or an estimated distance between the heart wall tissue and another tissue layer behind it, or an observed amount of gas formation. The selecting unit can calculate selection values, which are indicative of these aspects, and select a gated ultrasound image to be displayed based on the calculated selection values.

The selecting unit can also be adapted to select a composition of several gated ultrasound images, wherein a first part of the composition concerns the pre-ablation period, i.e. the first stage, including one or several gated images, a second part concerns the ablation period, i.e. the second stage, including one or several gated images being potentially other images than included by the first part, and the final part concerns the post-ablation period, i.e. the third stage, including one or several gated images being potentially other images than included by the first part and/or the second part. The selecting unit can provide a graphical user interface for allowing a physician to select the different gated ultrasound images for such image composition on the basis of the physician's visual inspection, or the selecting unit can be adapted to use an algorithm that automatically interprets the data. Preferentially, the algorithm calculates selection values as described above and applies selection rules to the selection values for automatically selecting one or several gated ultrasound images.

Although in the above embodiments the phase signal is preferentially a cardiac trigger signal, the phase signal can also be a respiratory trigger signal. Moreover, the phase signal providing unit can provide several phase signals, for instance, a cardiac trigger signal and a respiratory trigger signal, wherein based on these signals different motion phases can be defined, to which the generated ultrasound signals can be assigned. For instance, if the phase signal providing unit provides a cardiac trigger signal and a respiratory trigger signal, several cardiac motion phases and several respiratory motion phases can be defined, wherein each provided ultrasound signal, i.e. preferentially each A-line, can be assigned to a cardiac motion phase and a respiratory motion phase and wherein for each combination of a cardiac motion phase and a respiratory motion phase a gated ultrasound image can be generated based on the ultrasound signals assigned to the respective motion phases.

Although in the embodiment described above with reference to FIG. 2 the catheter tip comprises a single ultrasound transducer only, in another embodiment the catheter tip can also comprise two or more ultrasound transducers. Preferentially, different ultrasound transducers can acquire different A-lines, which can be used for generating different sets of gated M-mode images. The selecting unit can then be adapted to apply the above described selection procedure on all gated ultrasound images of all different sets of gated ultrasound images. For example, during ablation that particular gated M-mode image of all gated M-mode images of all ultrasound transducers may be chosen that shows the maximum degree of transmurality. The different ultrasound transducers preferentially send and receive the ultrasound in different directions.

Procedures, which have been described above with respect to A-lines, can also be performed with A-line envelopes and vice versa.

Although in the above described embodiments certain selection criteria, in particular certain selection values, for selecting one or several gated ultrasound images to be displayed have been described, in other embodiments also other selection criteria can be used for selecting one or several gated ultrasound images, in particular, depending on the respective desired application.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like assigning procedures for assigning a motion phase to a provided ultrasound signal, ultrasound images generation procedures for generating ultrasound images based on the ultrasound signals, selection procedures for selecting ultrasound images from the generated ultrasound images, et cetera performed by one or several units or devices can be performed by any other number of units or devices. For instance, steps 103 to 105 can be performed by a single unit or by any other number of different units. The procedures and/or the control of the imaging system in accordance with the imaging method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an imaging system for imaging a periodically moving object. An assigning unit assigns ultrasound signals like A-lines to motion phases based on a provided phase signal, wherein an ultrasound images generation unit generates several ultrasound images like gated M-mode images for the different motion phases based on the ultrasound signals assigned to the respective motion phase. A selecting unit is used to select an ultrasound image from the generated ultrasound images, wherein a display unit displays the selected ultrasound image. The selected ultrasound image corresponds therefore to a single motion phase only such that motion artifacts in the displayed ultrasound image are reduced. The imaging system is particularly useful for, for instance, monitoring cardiac ablation procedures.

The invention claimed is:

1. An imaging system for imaging a periodically moving object, the imaging system comprising:
   an ultrasound signals providing unit for providing ultrasound signals being A-lines of the object for different times,
   a phase signal providing unit for providing a phase signal being indicative of motion phases of a periodic movement of the object at the different times,
   an assigning unit for assigning the A-lines to the motion phases based on the provided phase signal,
   an ultrasound images generation unit for generating a plurality of ultrasound images being M-mode images respectively corresponding to the motion phases, wherein each M-mode image is generated based on the A-lines assigned to the respective corresponding motion phase, a selecting unit for selecting an ultrasound image from the generated ultrasound images, and a display unit for displaying the selected ultrasound image.

2. The imaging system as defined in claim 1, wherein the selecting unit is adapted to determine selection values for the generated ultrasound images, wherein a selection value is determined based on image values of the respective ultrasound images, and to apply selection rules to the selection values for selecting the ultrasound image from the generated ultrasound images.

3. The imaging system as defined in claim 2, wherein the object is a tissue wall, and the imaging system further comprises an energy application unit for applying energy to the tissue wall for influencing the tissue wall, and wherein the ultrasound signals providing unit is adapted to provide ultrasound signals of the tissue wall for the different times, and the selecting unit is adapted to determine at least one of the following selection values:
a first distance value being indicative of a distance between a sensing probe used for measuring the ultrasound signals and the tissue wall,
a wall thickness value being indicative of a thickness of the tissue wall,
a transmurality value being indicative of a part of the tissue wall having been influenced by the application of energy,
a second distance value being indicative of a distance between the tissue wall and an element behind the tissue wall, and
a gas formation value being indicative of an amount of gas formed in the tissue wall.

4. The imaging system as defined in claim 3, wherein the selecting unit is adapted to select the ultrasound image, for which at least one of the following values has been determined: a smallest first distance value, an average first distance value, a smallest wall thickness value, a largest transmurality value, a largest second distance value, a smallest second distance value and a largest gas formation value.

5. The imaging system as defined in claim 3, wherein the energy is applied to the tissue wall in accordance with an energy application procedure having different stages, and wherein the selecting unit is further adapted to select the ultrasound image from the generated ultrasound images based on a current stage of the energy application procedure in addition to the selection values.

6. The imaging system as defined in claim 5, wherein the selection rules define that:
in a first stage, before applying energy to the object, firstly an ultrasound image is selected, for which an average first distance value has been determined, and secondly an ultrasound image is selected, for which the smallest wall thickness value has been determined,
in a second stage, during applying energy to the object, at least one of an ultrasound image, for which the largest transmurality value has been determined, and an ultrasound image, for which the largest gas formation value has been determined, is selected, and
in a third stage, after applying energy to the object, an ultrasound image, for which the largest transmurality value has been determined, is selected.

7. The imaging system as defined in claim 1, wherein the periodic movement of the object comprises a plurality of motion periods, and each motion period comprises a plurality of motion phases, and wherein the assigning unit further assigns ultrasound signals in a selected motion period of the plurality of motion periods to the motion phases of the selected motion period based on a phase signal provided for a previous motion period of the plurality of motion periods occurring before the selected motion period.

8. The imaging system as defined in claim 1, wherein the ultrasound signals providing unit is adapted to apply an envelope detection procedure on the A-lines and to provide the resulting A-line envelopes as the ultrasound signals.

9. The imaging system as defined in claim 1, wherein the object is a region of a living being and wherein the phase signal providing unit is adapted to provide at least one of a cardiac motion signal being indicative of cardiac motion and a respiratory motion signal being indicative of respiratory motion as the phase signal.

10. The imaging system as defined in claim 1, wherein the phase signal providing unit is adapted to determine the phase signal from the ultrasound signals and to provide the determined phase signal.

11. The imaging system as defined in claim 1, further comprising a sensing probe, in which the ultrasound signals providing unit and an energy application unit for applying energy to the object are integrated.

12. An imaging method for imaging a periodically moving object, the imaging method comprising:
providing ultrasound signals being A-lines of the object for different times by an ultrasound signals providing unit,
providing a phase signal being indicative of motion phases of a periodic movement of the object at the different times by a phase signal providing unit,
assigning the ultrasound signals to the motion phases based on the provided phase signal by an assigning unit,
generating a plurality of ultrasound images being M-modes images respectively corresponding to the motion phases by an ultrasound images generation unit, wherein each M-mode image is generated based on the A-lines assigned to the respective corresponding motion phase,
selecting an ultrasound image from the generated ultrasound images by a selecting unit, and
displaying the selected ultrasound image by a display unit.

13. A non-transitory computer readable medium, having stored thereon a program that, when executed by a computer, causes the computer to image a periodically moving object by:
receiving ultrasound signals, comprising A-lines of the object for different times;
receiving, from a phase signal providing unit, a phase signal being indicative of motion phases of a periodic movement of the object at the different times;
assigning the ultrasound signals to the motion phases based on the provided phase signal;
generating a plurality of ultrasound images, comprising M-modes images respectively corresponding to the motion phases, wherein each M-mode image is generated based on the A-lines assigned to the respective corresponding motion phase;
selecting an ultrasound image from the generated ultrasound images; and
causing the selected ultrasound image to be displayed on a display.

* * * * *